United States Patent [19]
Palmer et al.

[11] Patent Number: 5,718,359
[45] Date of Patent: Feb. 17, 1998

[54] SURGICAL STAPLER WITH LOCKOUT MECHANISM

[75] Inventors: Mitchell J. Palmer, New Milford, Conn.; Richard C. McClure, Claremont, Calif.

[73] Assignee: United States of America Surgical Corporation, Norwalk, Conn.

[21] Appl. No.: 514,636

[22] Filed: Aug. 14, 1995

[51] Int. Cl.$^6$ .................................. A61B 17/068
[52] U.S. Cl. .................. 227/175.2; 227/19; 227/175.4; 227/176.1
[58] Field of Search ..................... 227/175.1, 175.2, 227/175.3, 175.4, 176.1, 19

[56] References Cited

U.S. PATENT DOCUMENTS

| | | |
|---|---|---|
| Re. 34,519 | 1/1994 | Fox et al. . |
| 2,174,219 | 9/1939 | Balma . |
| 2,246,647 | 6/1941 | Vancura et al. . |
| 3,079,606 | 3/1963 | Bobrov et al. . |
| 3,490,675 | 1/1970 | Green et al. . |
| 3,499,591 | 3/1970 | Green . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,304,236 | 12/1981 | Conta et al. . |
| 4,391,401 | 7/1983 | Moshofsky . |
| 4,429,695 | 2/1984 | Green . |
| 4,473,077 | 9/1984 | Noiles et al. . |
| 4,519,532 | 5/1985 | Foslien . |
| 4,520,817 | 6/1985 | Green . |
| 4,569,346 | 2/1986 | Poirier . |
| 4,576,165 | 3/1986 | Green et al. . |
| 4,576,167 | 3/1986 | Noiles . |
| 4,591,085 | 5/1986 | DiGiovanni . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,809,898 | 3/1989 | Gassner et al. . |
| 4,863,088 | 9/1989 | Redmond et al. . |
| 4,892,244 | 1/1990 | Fox et al. . |
| 4,955,959 | 9/1990 | Tompkins et al. . |
| 5,031,814 | 7/1991 | Tompkins et al. . |
| 5,083,695 | 1/1992 | Foslien et al. . |
| 5,141,144 | 8/1992 | Foslien et al. . |
| 5,156,614 | 10/1992 | Green et al. . |
| 5,366,133 | 11/1994 | Geiste . |
| 5,413,267 | 5/1995 | Solyntjes et al. . |
| 5,415,335 | 5/1995 | Knodell, Jr. . |
| 5,445,304 | 8/1995 | Plyley et al. . |
| 5,458,279 | 10/1995 | Plyley . |
| 5,462,215 | 10/1995 | Viola et al. . |
| 5,465,896 | 11/1995 | Allen et al. . |
| 5,470,006 | 11/1995 | Rodak . |
| 5,470,008 | 11/1995 | Rodak . |
| 5,470,009 | 11/1995 | Rodak . |

FOREIGN PATENT DOCUMENTS 0365153  8/1995  European Pat. Off. .

*Primary Examiner*—Scott A. Smith

[57] ABSTRACT

An apparatus for applying surgical fasteners is disclosed which includes a first lockout mechanism configured to prevent premature ejection of fasteners during shipment, and a second lockout mechanism to prevent reactuation of the apparatus after it has once been actuated.

24 Claims, 10 Drawing Sheets

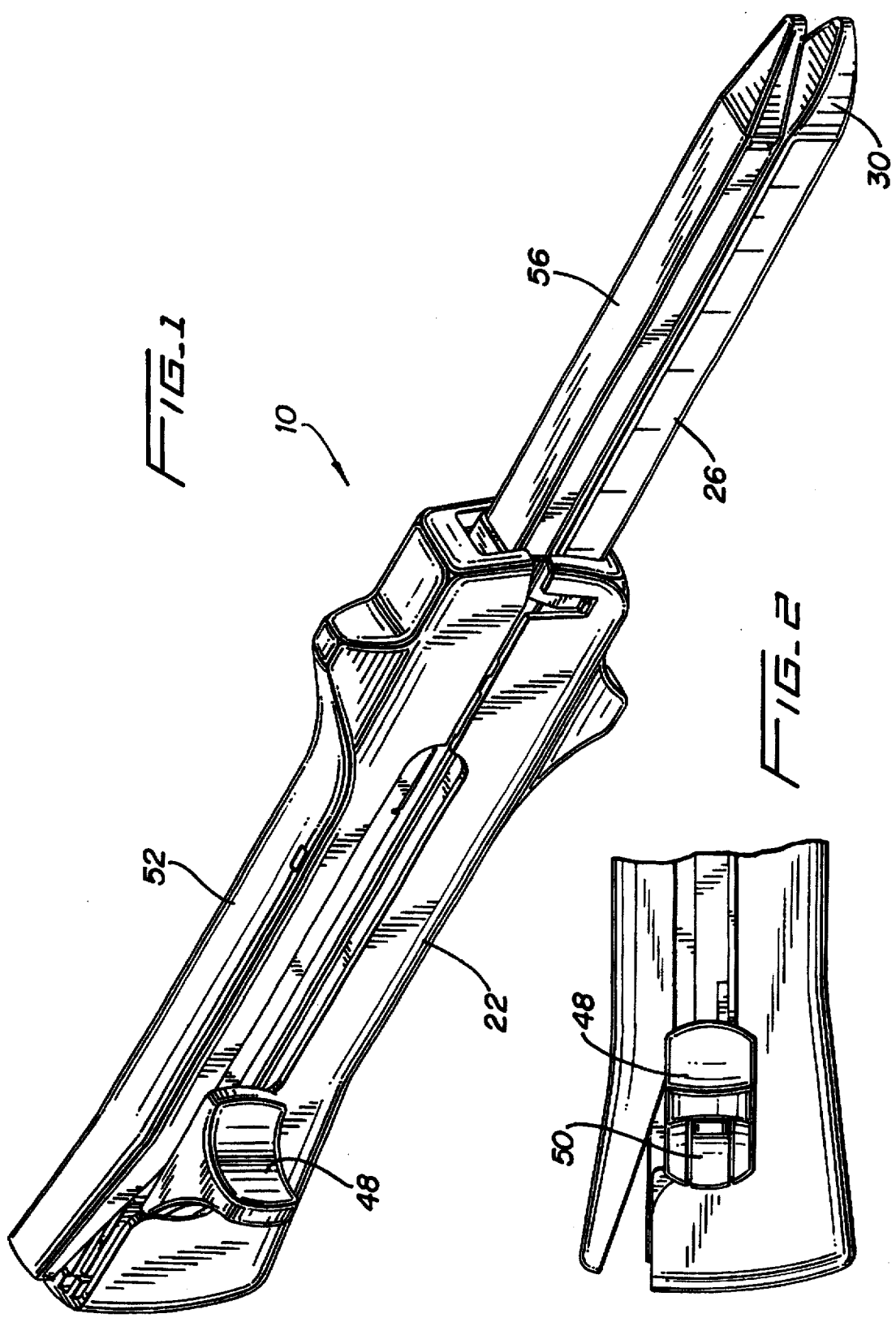

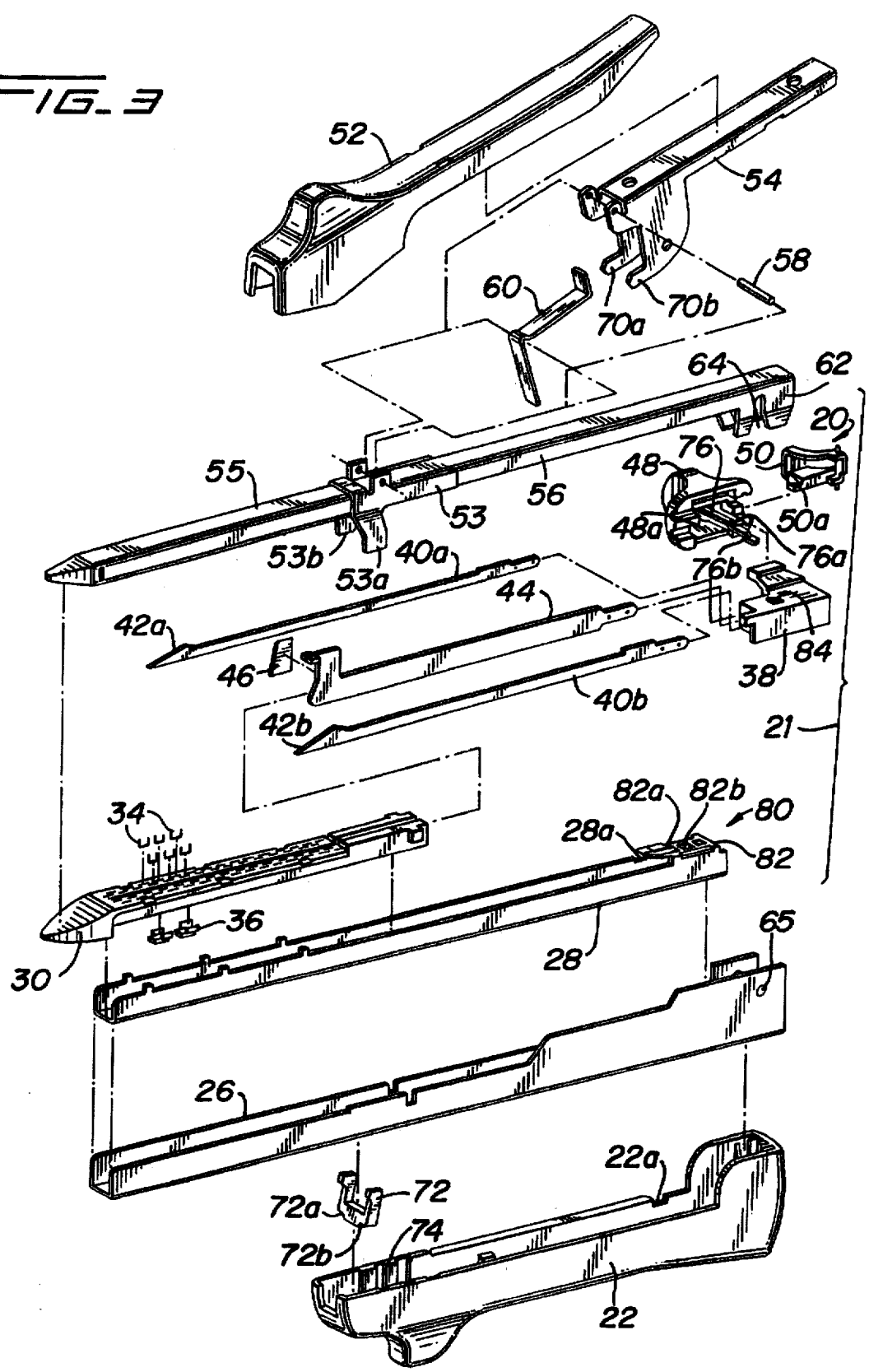

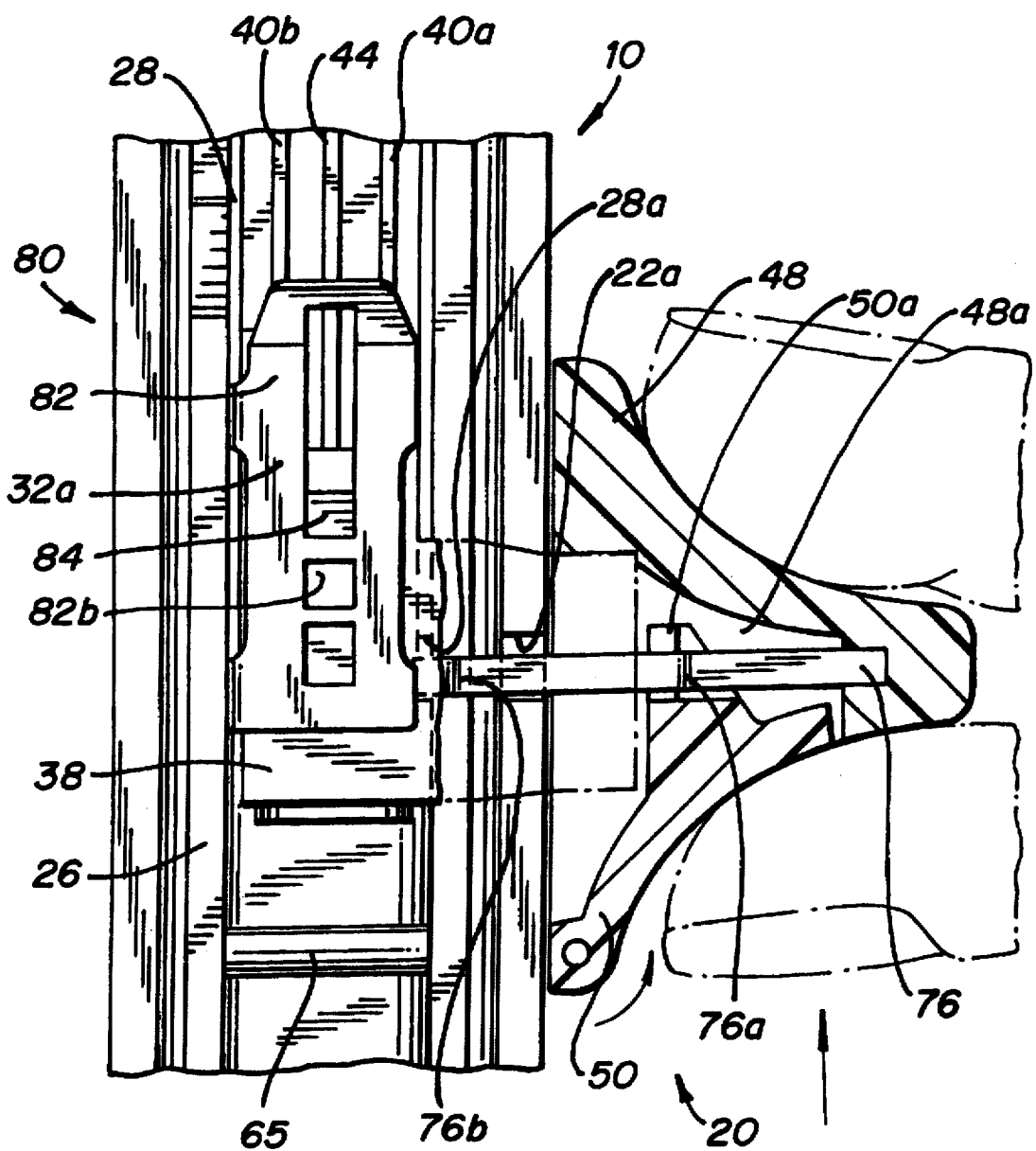

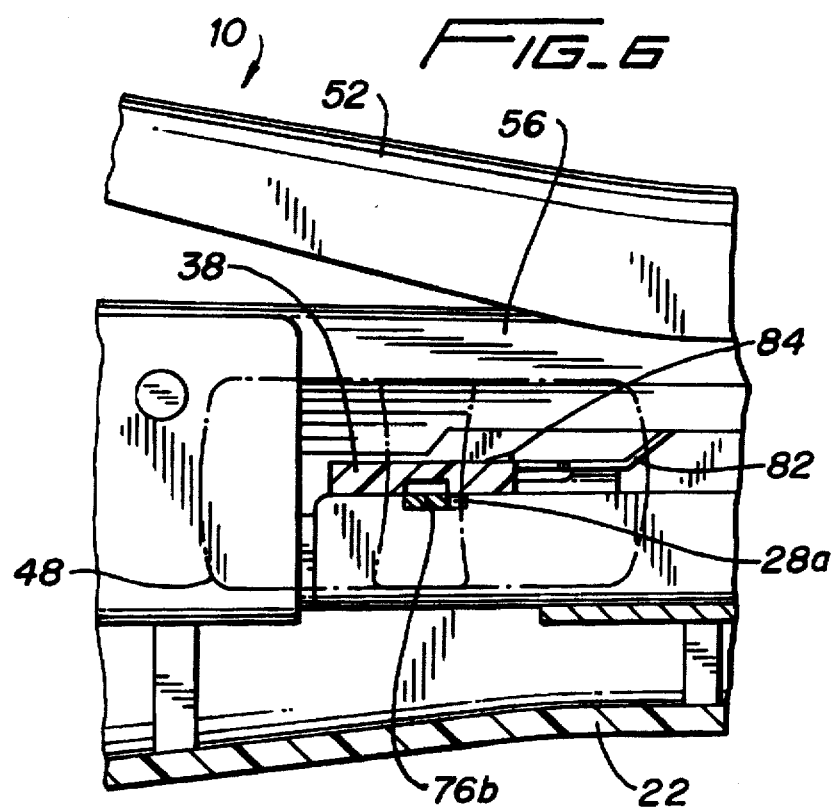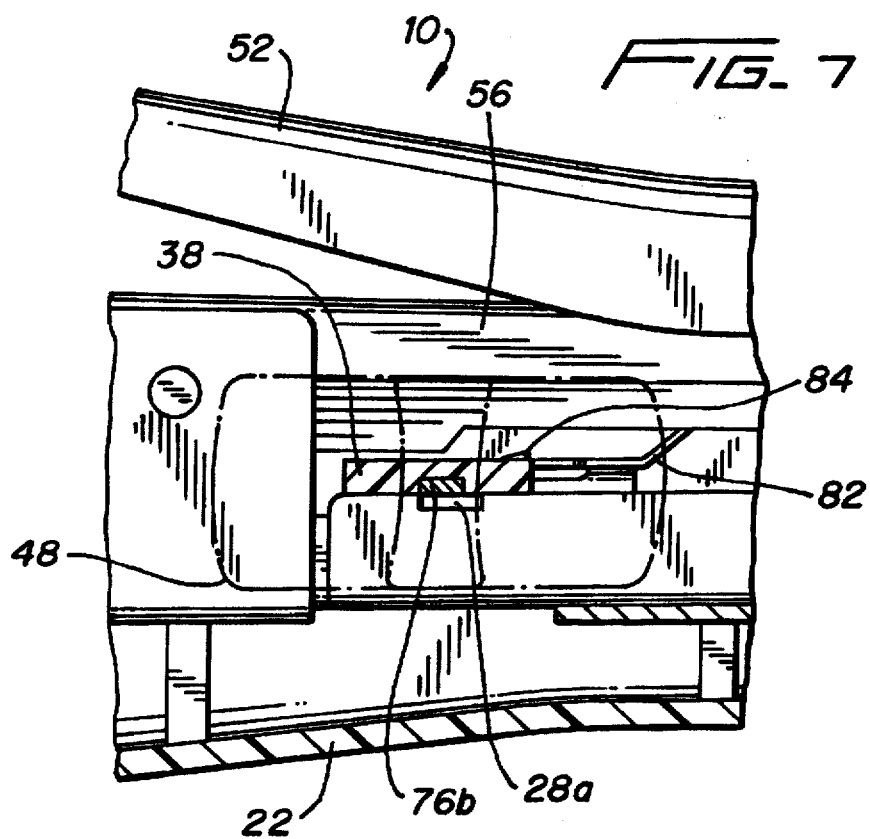

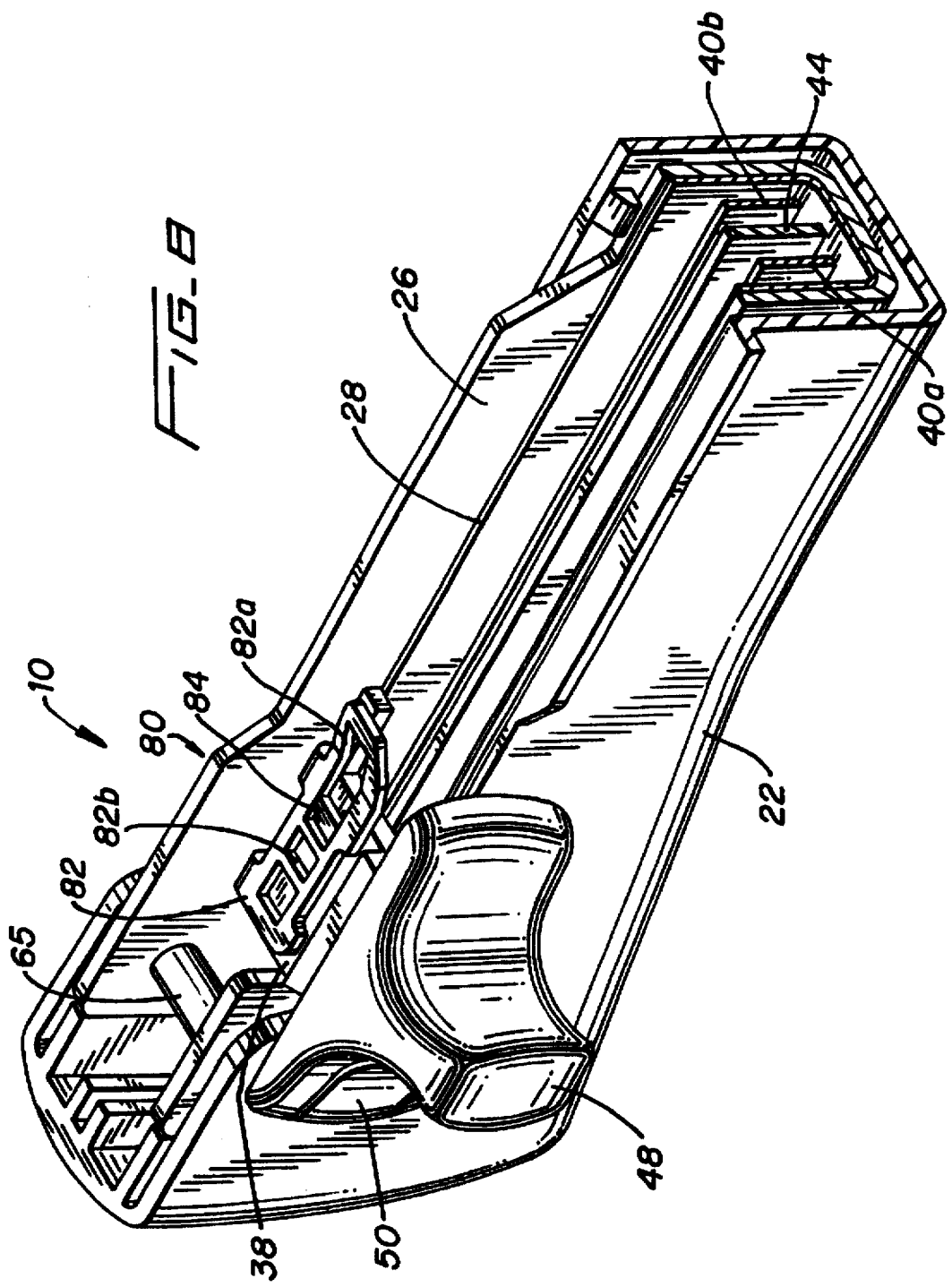

FIG_10

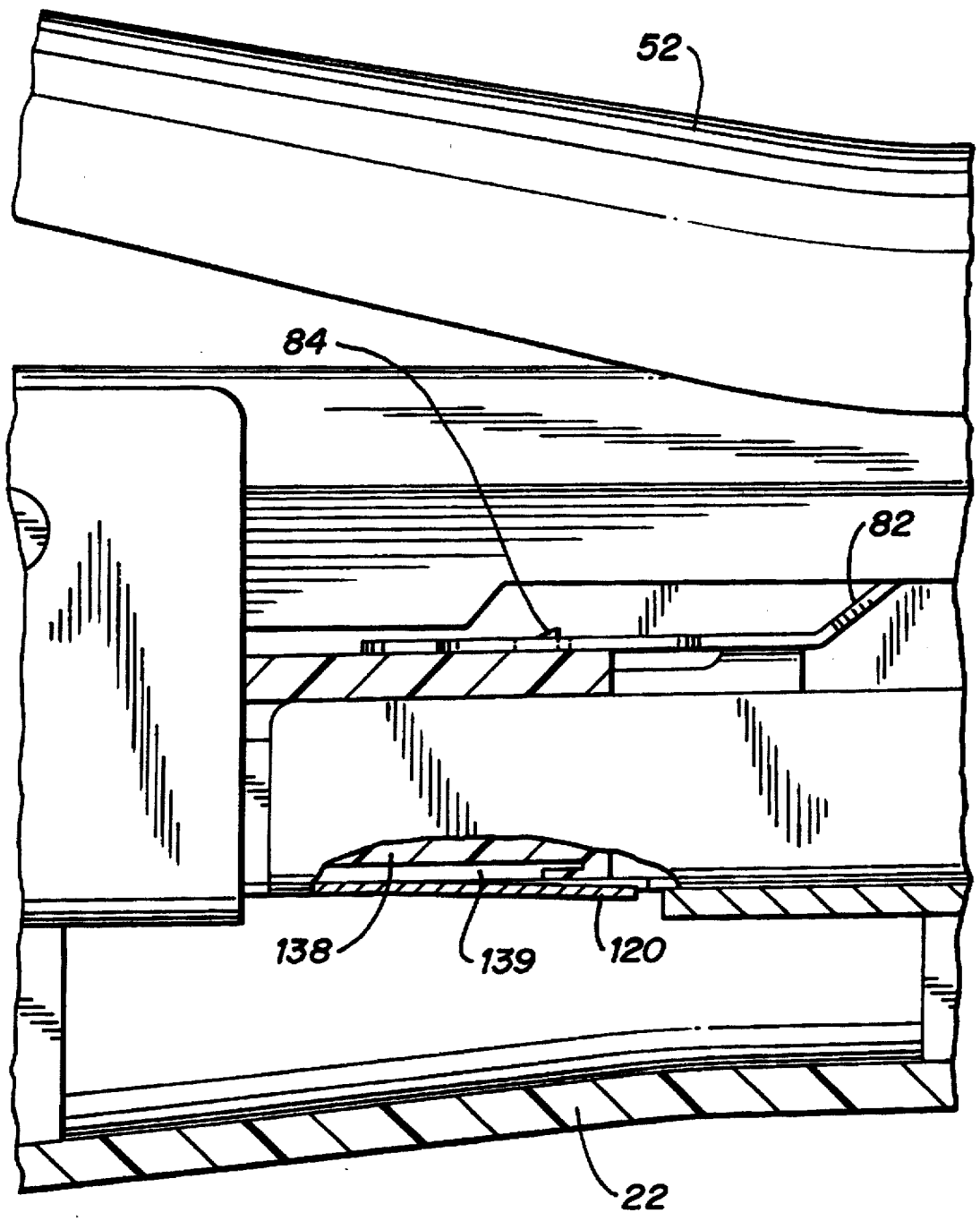
FIG_12

SURGICAL STAPLER WITH LOCKOUT MECHANISM

BACKGROUND

1. Technical Field

This application relates to surgical staplers, and more particularly, to an apparatus for sequentially applying a plurality of surgical fasteners to body tissue and a lockout mechanism therefor.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of staples arranged in at least two lateral rows while the other member comprises an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695, 5,065,929, and 5,156,614.

Surgical staplers which employ lockout mechanisms to prevent reactuation after firing are also known and are disclosed, for example, in U.S. Pat. No. 4,955,959. Other staplers having a lockout mechanism are disclosed in U.S. Pat. Nos. Re. 34,519, 5,129,570, 5,156,315 and 5,253,793. The lockout mechanism prevents the refiring of a spent staple cartridge when the cartridge remains loaded within the surgical apparatus. Because the mechanism is actuable only after the stapler has been fired, it is ineffective to prevent premature firing of the stapler during shipment.

A surgical stapler employing a shipping interlock is disclosed in U.S. Pat. No. 5,366,133, the disclosure of which is herein incorporated by reference, which prevents premature actuation of the apparatus by jostling and vibrations normally occurring during shipment of the apparatus from the manufacturer to the user and during handling by the user.

The present application discloses an improved lockout mechanism which prevents premature ejection of staples during shipment and an improved lockout mechanism which prevents refiring of the stapler when the stapler is loaded with a spent or partially spent cartridge.

SUMMARY

The subject application is directed to a surgical stapling apparatus that has a mechanism configured to prevent premature actuation of the apparatus during shipment and handling, and a lockout assembly configured to prevent refiring of the apparatus. The apparatus includes a cartridge supporting portion having a cartridge positioned therein which contains a plurality of surgical fasteners and a plurality of fastener pushers configured to eject the surgical fasteners from the cartridge. An anvil supporting portion defines an anvil surface against which the surgical fasteners are driven when they are ejected from the cartridge. A cam bar retainer retains at least two cam bars configured to sequentially interact with the pushers as the cam bar retainer translates longitudinally (distally) from a pre-fired position. An actuator knob is mounted to the cam bar retainer for facilitating translation of the cam bar retainer.

A shipping lock is operatively associated with the actuator knob to maintain the cam bar retainer in the pre-fired position, i.e. during shipment and handling, and thereby prevent premature ejection of fasteners from the cartridge. The shipping lock includes a pivotable release button mounted within the actuator knob and connected to a retention bar that releasably engages a keeper notch provided in the cartridge supporting portion. A second locking mechanism is provided to prevent the apparatus from being actuated after it has been actuated. The second locking mechanism includes a ramped tab formed on the cam bar retainer which is configured to engage an aperture defined in a clasp provided on the cartridge supporting portion when the cam bar retainer is retracted to a post-fired proximal position.

BRIEF DESCRIPTION OF THE DRAWINGS

Various embodiments of the surgical apparatus of the subject application will be described hereinbelow with reference to the drawings wherein:

FIG. 1 is a perspective view of a surgical stapling apparatus constructed in accordance with a preferred embodiment of the subject application;

FIG. 2 is a localized side elevational view of the surgical stapling apparatus of FIG. 1 illustrating the actuator knob having the release button;

FIG. 3 is an exploded perspective view of the surgical stapling apparatus illustrated in FIG. 1;

FIG. 5 is a top plan view of the cartridge supporting portion with the actuator knob in cross-section to illustrate the release button in an unlocked position;

FIG. 6 is a localized side elevational view in cross-section of the surgical apparatus of FIG. 1 with the shipping lockout mechanism illustrated in the position shown in FIG. 4;

FIG. 7 is a localized side elevational view in cross-section of the surgical apparatus of FIG. 1 with the shipping lockout mechanism illustrated in the position shown in FIG. 5;

FIG. 8 is an enlarged perspective view of a section of the cartridge supporting portion illustrating the firing lockout mechanism in a pre-fired position.

FIG. 12 is a localized side view in cross-section showing the shipping lockout mechanism of FIG. 10 in the release position and the cam bar retainer in a post-fired position.

DETAILED DESCRIPTION OF PREFERRED EMBODIMENTS

Figure 4:
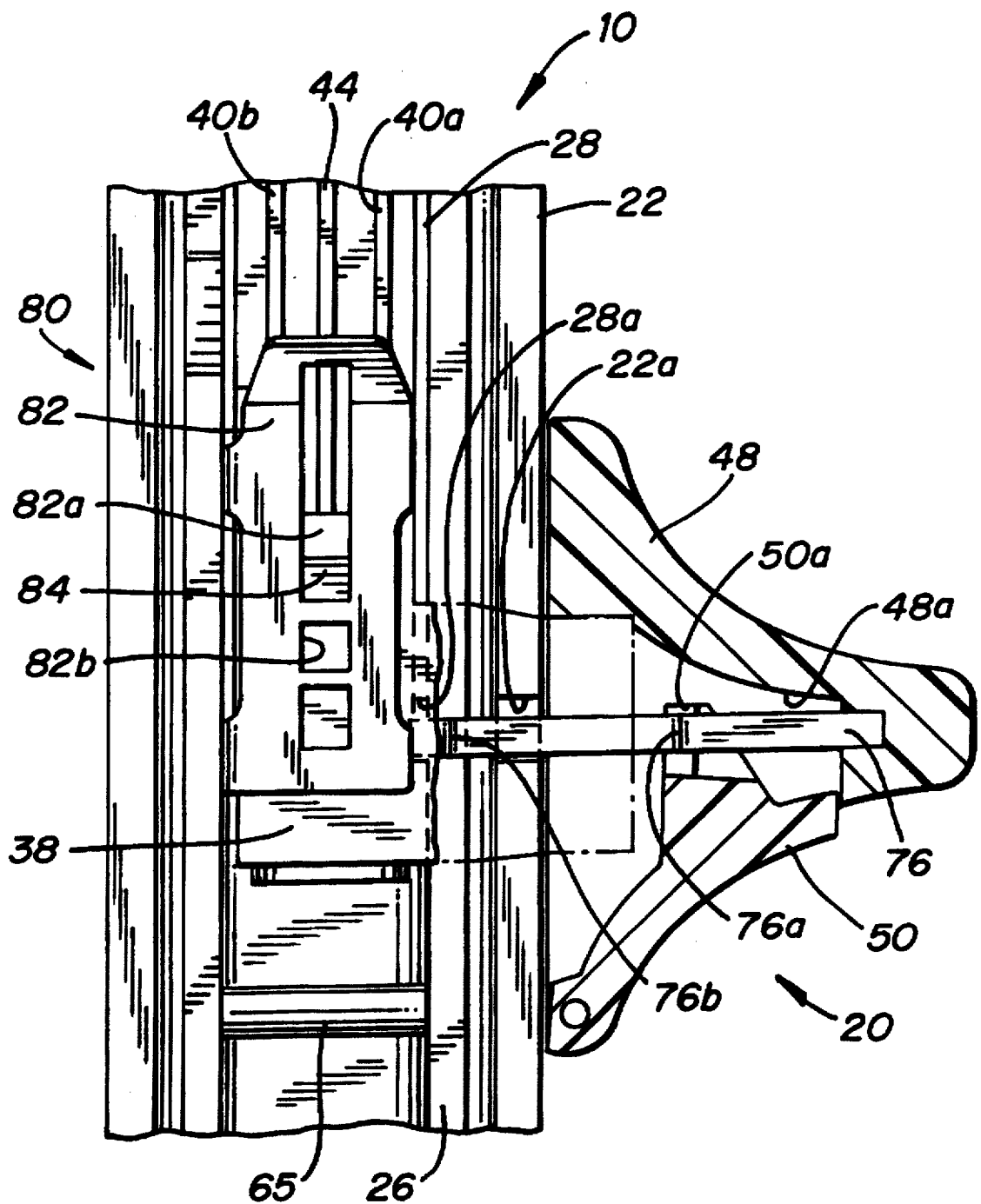
FIG. 4 is a top plan view of the cartridge supporting portion of the surgical stapling apparatus of FIG. 1 with the actuator knob in cross-section to illustrate the release button in a locked position.

In the drawings and in the description which follows, the term "proximal", as is traditional, will refer to the end of the apparatus which is closer to the operator, while the term "distal" will refer to the end of the apparatus which is further from the operator.

Referring now to the drawings wherein like reference numerals identify similar structural elements disclosed herein, there is illustrated in FIG. 1 a surgical stapling apparatus constructed in accordance with a preferred embodiment of the subject application and designated generally by reference numeral 10. Surgical apparatus 10 is a linear stapling device configured to sequentially apply a plurality of surgical fasteners to body tissue and preferably concomitantly form an incision in the stapled tissue.

Figure 9:
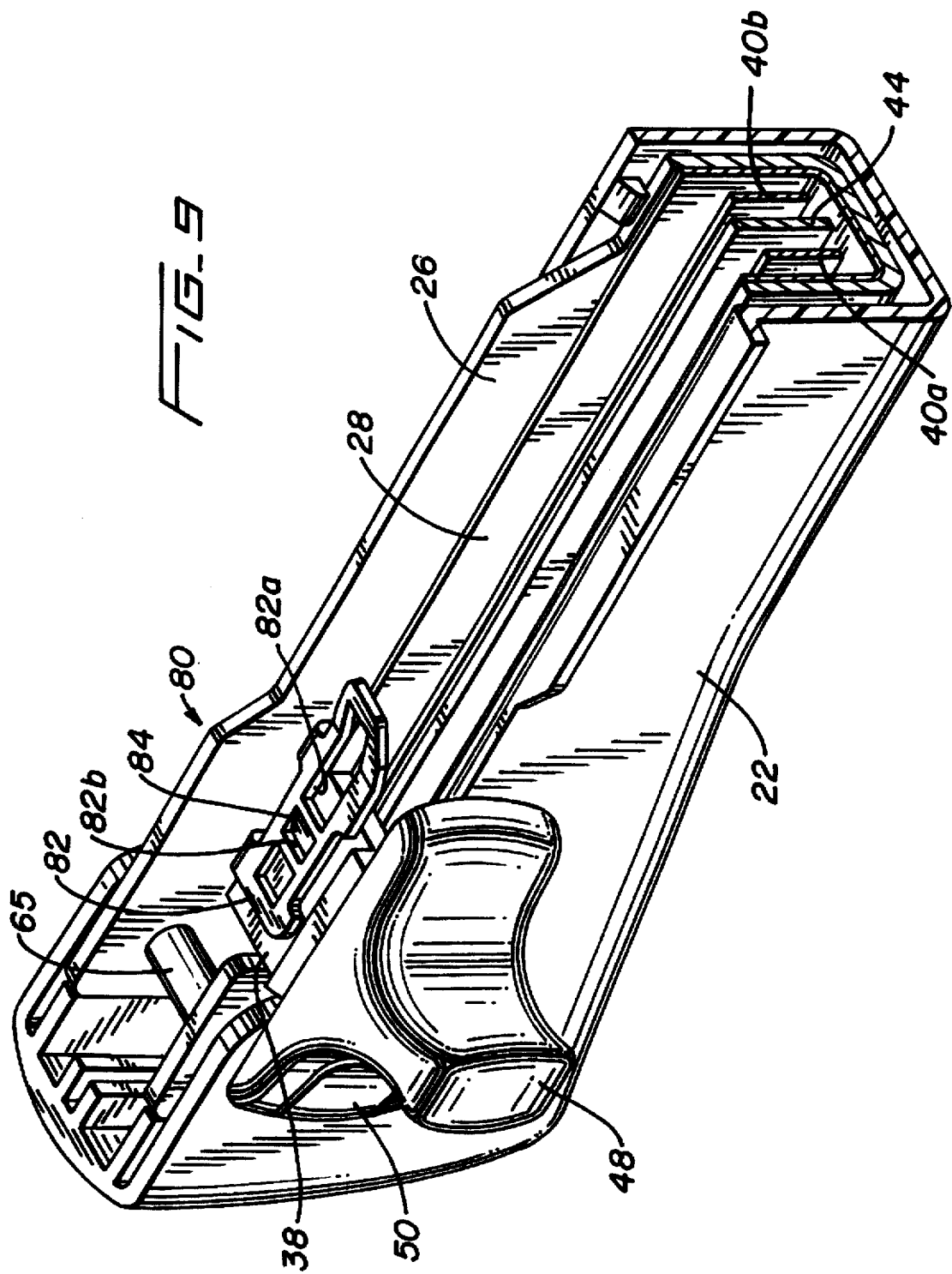
FIG. 9 is an enlarged perspective view of a section of the cartridge supporting portion of the surgical apparatus of FIG. 1 illustrating the firing lockout mechanism in a post-fired position.

In accordance with the subject application, surgical apparatus 10 is provided with a first lockout mechanism designated generally by reference numeral 20 and illustrated in FIGS. 4 and 5, which prevents premature actuation of the apparatus during shipment and handling, and a second lockout mechanism designated generally by reference numeral 80 and illustrated in FIGS. 3, 8 and 9, which prevent refiring of the apparatus after a stapling operation. The operation and construction of both lockout mechanisms is described in greater detail hereinbelow.

Referring now to FIG. 3, the structural elements of surgical apparatus 10 are illustrated in detail, including the elements which define lockout mechanisms 20 and 80. Surgical apparatus 10 includes a lower body portion or housing 22 having an elongated cartridge support channel 26 mounted therein. Support channel 26 is dimensioned and configured to receive and detachably support a disposable loading unit, designated generally by reference numeral 21. Disposable loading unit 21 includes an elongated carrier channel 28, a cartridge 30 mounted in a distal portion of carrier channel 28, an actuator or firing knob 48, and a cam bar retainer 38 supporting a pair of elongated cam bars 40a, 40b and a blade carrier 44. Cartridge 30 houses a plurality of surgical fasteners 34 and a plurality of pushers or drivers 36 configured to eject the fasteners from the cartridge when acted upon by an applied driving force. An example of a staple pusher in accordance with the subject application is disclosed in U.S. Pat. No. 4,978,049, the disclosure of which is herein incorporated by reference.

Angled cam surfaces 42a and 42b of cam bars 40a, 40b interact with pushers 36 as the cam bar retainer 38 is moved relative to carrier channel 28 during a fastener applying operation. This interaction is described in detail in U.S. Pat. No. 4,978,049. Blade carrier 44 is disposed between cam bars 40a and 40b and carries a knife blade 46 configured to form an incision in the body tissue between the rows of staples.

With continued reference to FIG. 3, surgical apparatus 10 further includes an upper body portion 52 housing a clamping channel 54 and an elongated anvil support channel 56. The distal portion of channel 56 defines an anvil 55 having a fastener forming surface against which the legs of the surgical fasteners 34 are formed when they are ejected from cartridge 30 (see, for example, U.S. Pat. No. 4,608,981). A pivot pin 58 operatively connects clamping channel 54 to tissue stop 53 of anvil support channel 56. A leaf spring 60 is provided for biasing the clamping channel 54 and upper body 52 about pivot pin 58 away from anvil support channel 56. A mounting flange 62 having a reception groove 64 is formed at the proximal end of anvil support channel 56 for detachably engaging a mounting pin 65 disposed at the proximal end of cartridge support channel 26. Fingers 53a, 53b of tissue stop 53 depend from anvil support channel 56 for facilitating lateral alignment of anvil support channel 56 and cartridge support channel 26 when the two structures are approximated during assembly.

Clamping channel 54 includes a pair of distally extending clamping legs 70a and 70b which engage a clamp bracket 72 positioned in cartridge support channel 26, and retained within a correspondingly configured retention area 74 defined in lower body portion 22 of surgical apparatus 10. To effect approximation of the anvil support channel 56 and the cartridge support channel 26, i.e. to clamp body tissue therebetween, the upper body portion 52 is urged toward anvil support channel 56 to pivot clamping channel 54 about pivot pin 58 against the bias of leaf spring 60, such that clamping legs 70a and 70b engage the clamp surfaces 72a, 72b of clamp bracket 72. Continued pivotal movement of the upper body portion 52, causes camming interaction between clamping legs 70a and 70b and clamp surfaces 72a and 72b until anvil 55 and cartridge 30 are in substantial parallel alignment with one another. At such a time, surgical apparatus 10 can be actuated to sequentially apply a plurality of surgical fasteners to body tissue and concomitantly form an incision in the stapled tissue. The fasteners, as shown, are staples, however two part fasteners, including polymeric fasteners, can also be utilized.

Having described the overall construction and operation of surgical apparatus 10, the construction and operation of lockout mechanisms 20 and 80 will now be described. In particular, shipping lockout 20, which is illustrated in FIGS. 4–7, includes a pivoting release button 50 mounted within a cavity 48a defined in actuator knob 48 (see also, FIG. 2). A retention bar 76 is also supported within cavity 48a and is mounted in a cantilevered fashion to extend generally perpendicularly to the elongation of carrier channel 28. Retention bar 76 has a stepped construction which includes an intermediate section 76a that interacts with an angled camming surface 50a formed on release button 50. In use, pivotal movement of release button 50 causes corresponding movement of retention bar 76 as camming surface 50a contacts section 76a.

The distal section 76b of retention bar 76 is dimensioned and configured to interact with complimentary notches 22a and 28a defined in the side walls of lower body portion 22 and carrier channel 28, respectively (see also FIG. 3). More particularly, the distal section 76b is configured to releasably engage the notches during shipment of surgical apparatus 10 to inhibit movement of knob 48 and thereby prevent premature actuation of the apparatus. The engagement of distal section 76b in notches 22a, 28a inhibits both proximal and distal movement of cam bar retainer 38 to maintain it in the pre-fired proximal position of FIG. 8. During use however, the distal section 76b of retention bar 76 is displaced from the notches, and knob 48 is freely movable by the user to actuate surgical apparatus 10, as discussed previously hereinabove. To displace retention bar 76, release button 50 is pivoted from the shipping position illustrated in FIG. 4 to the release position illustrated in FIG. 5. As a result, the distal section 76b of retention bar 76 is moved from a locked position, engaged within notch 28a, as illustrated in FIG. 6, to the released position, spaced from notch 28a, as illustrated in FIG. 7. That is, camming surface 50a cams retention bar 76 slightly upwardly such that distal section 76b is likewise cammed upwardly out of notch 28a to allow free movement of knob 48.

The second lockout mechanism 80, which is most clearly illustrated in FIGS. 8 and 9, is specifically adapted to prevent reactuation of surgical apparatus 10 after actuation and more particularly after the user has drawn knob 48 proximally after actuating the stapler. Lockout mechanism 80 includes a retention clasp 82 which is formed integral with carrier channel 28 and which has a retention slot or aperture 82b and a release slot or aperture 82a defined therein. A ramped detent 84 projects from cam bar retainer 38 and interacts with retention clasp 82. In particular, when cam bar retainer 38 is in the pre-fired proximal position illustrated in FIG. 8, detent 84 projects into release slot 82a and is disposed therein until knob 48 is moved distally to actuate the apparatus. After the apparatus has been actuated and knob 48 is moved proximally to draw cam bar retainer 38 to the post-fired proximal position illustrated in FIG. 9, ramped detent 84 is urged into engagement with retention slot 82b and is lockingly retained therein, thereby preventing reactuation of surgical apparatus 10. In this lockout position, the apparatus cannot be refired until such time the disposable loading unit 21 is removed from support channel 26 and replaced with a disposable loading unit having a cartridge containing staples.

In use, prior to actuation, cam bar retainer 38 and actuator knob 48 are in the pre-fired proximal position of FIG. 8 with detent 84 positioned in release slot 82a of clasp 82. In this position, distal section 76b of retention bar 76 is positioned within notches 22a and 28a of lower body portion 22 and carrier channel 28. Thus, retention bar 76 prevents premature distal movement of actuator 48 (and cam bar retainer 38). Retention bar 76 also prevents proximal movement of actuator 48, to thereby maintain cam bar retainer 38 in a pre-fired proximal position which is distal of the post-fired proximal position.

To fire the staples, actuator knob 48 is grasped by the surgeon and release button 50 is pressed inwardly to disengage retention bar 76 from notches 22a, 28a. Release button 50 is preferably advantageously positioned on knob 48 such that the surgeon's grip on knob 48 to fire the staples automatically presses release button 50 inwardly to release retention bar 76. When actuator knob 48 is slid distally, cam bar retainer 38 is also slid distally carrying cam bars 40a, 40b into engagement with staple pushers 36 to sequentially apply staples 34 to the body tissue clamped between the fastener forming surface of anvil 55 and the cartridge 30. As cam bar retainer 38 moves distally, detent 84 slides out of release slot 82a. After the staples have been fired, actuator knob 48 is retracted proximally with the release button 50 remaining in its upwardly pressed position by the surgeon's thumb due to its advantageous positioning on the knob 48. Cam bar retainer 38 can then be retracted to its post-fired proximal position wherein detent 84 is in engagement with retention slot 82b. In this position the surgeon cannot advance the actuator 48 because of the abutment of detent 84 and the distal wall of slot 82b.

Figure 10:
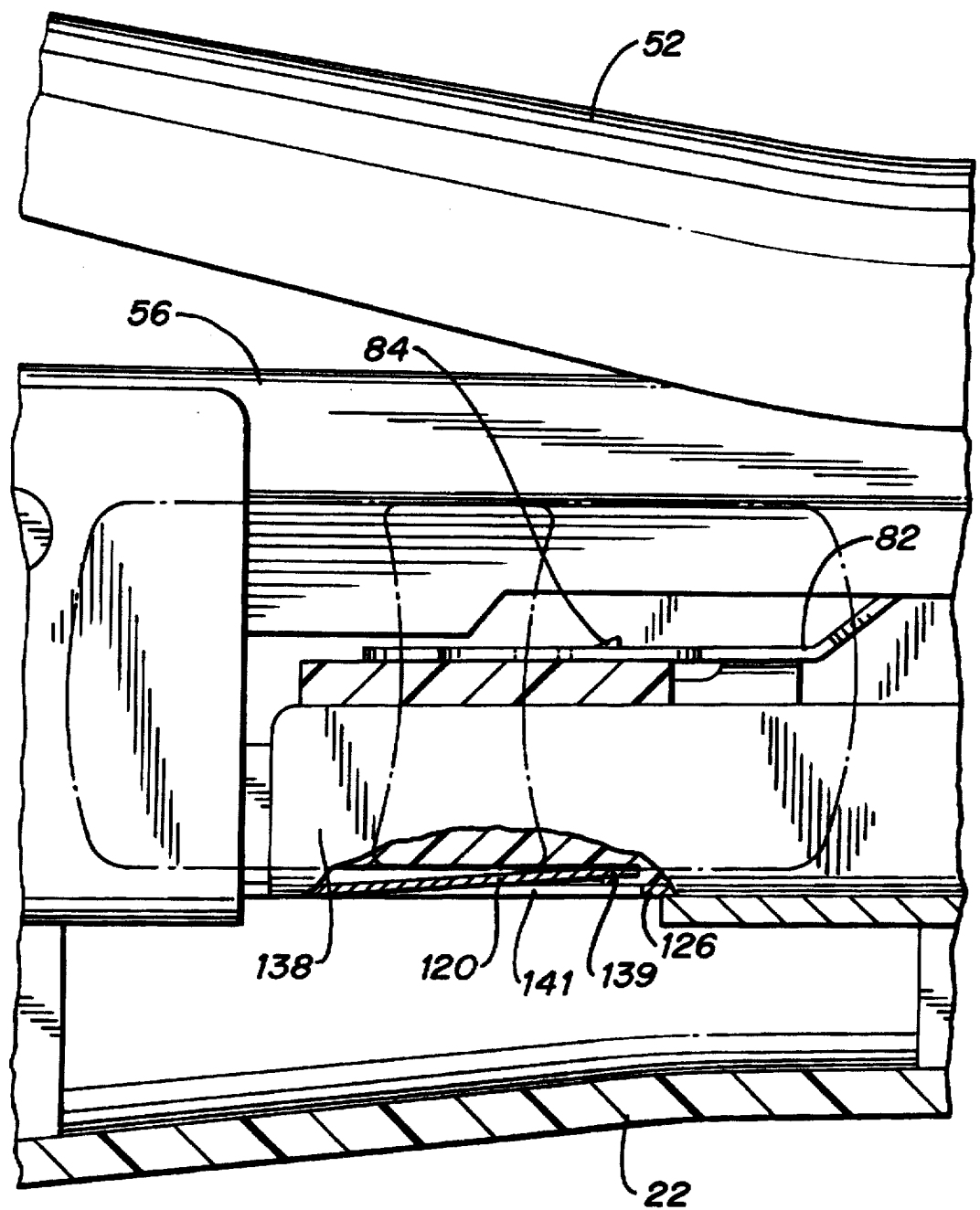
FIG. 10 is a localized side elevational view in cross-section of an alternate embodiment of the shipping lockout mechanism prior to actuation of the apparatus.
Figure 11:
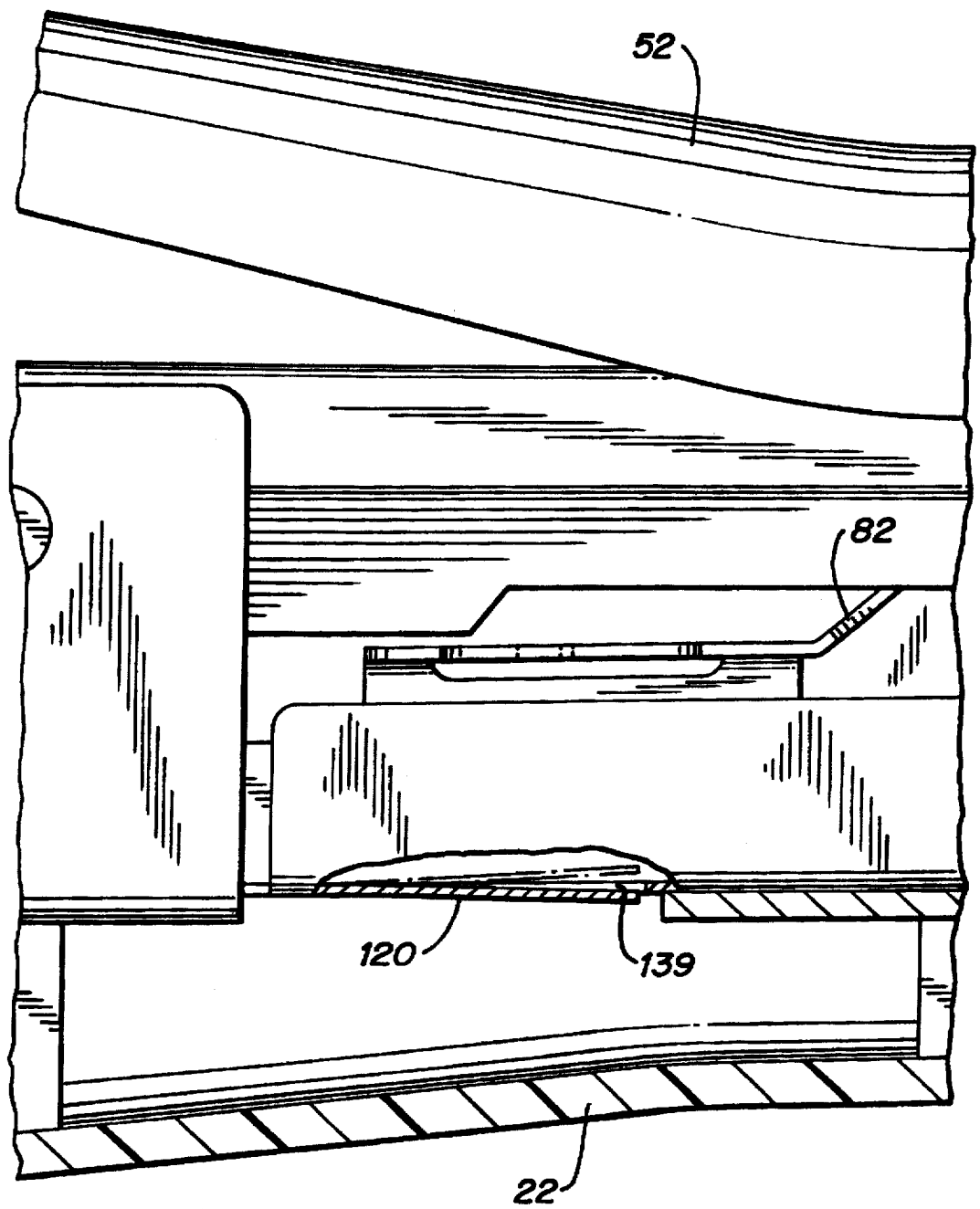
FIG. 11 is a localized side elevational view in cross-section showing movement of the shipping lockout mechanism of FIG. 10 to the release position.

FIGS. 10–12 illustrate an alternate embodiment of the shipping lockout mechanism. The staple refiring lockout is identical to that described above with respect to FIGS. 1–9. The shipping lockout is in the form of a leaf spring 120 which is normally biased to a downward position. Leaf spring 120 is attached to the cartridge support channel 126 and is shown in its initial position of FIG. 10 seated in a recess 139 of cam bar retainer 138. In this position, proximal movement of cam bar retainer 138 is prevented. Also, the frictional engagement between the leaf spring 120 in the recess 139 prevents distal movement of the cam bar retainer 138 during shipping and handling, i.e. until a sufficient force is applied by the user to advance the actuator knob of the stapler.

Upon distal movement of cam bar retainer 138 to fire the staples, leaf spring 120 is released from the recess 139 and returns to its normal position, biased through opening 141 below the plane of the cartridge support channel 126 as shown in FIG. 11. Consequently, the cam bar retainer 138 can be fully retracted on the return stroke to its proximal-most position to allow detent 84 to engage retention slot 82b in the manner described above. Thus, advancement of the actuator knob is prevented.

Although the subject application has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A surgical apparatus comprising:
   a) a cartridge supporting portion having a cartridge supported therein which contains a plurality of surgical fasteners and a plurality of pushers configured to eject the surgical fasteners from the cartridge;
   b) an anvil supporting portion relatively movable with respect to the cartridge supporting portion and having an anvil surface against which the surgical fasteners are driven when they are ejected from the cartridge;
   c) a cam bar retainer operatively associated with the cartridge and retaining at least two cam bars configured to sequentially interact with the pushers as the cam bar retainer translates distally from a pre-fired proximal position;
   d) an actuator connected to the cam bar retainer for facilitating the translation thereof;
   e) a first locking member extending from the actuator and configured to releasably engage a notch provided in the cartridge supporting portion to maintain the cam bar retainer in the pre-fired proximal position; and
   f) a second locking member supported on the cam bar retainer and configured to engage an aperture provided within the cartridge supporting portion upon retraction of the cam bar retainer to a post-fired proximal position.

2. A surgical apparatus as recited in claim 1, further comprising an elongated carrier channel supported within the cartridge supporting portion and carrying the cartridge, the cam bar retainer, and the cam bars.

3. A surgical apparatus as recited in claim 2, wherein the first locking member includes a retention bar which cooperates with a release button pivotably mounted to the actuator.

4. A surgical apparatus as recited in claim 3, wherein the release button has a camming surface configured to displace the retention bar to release the retention bar from the notch.

5. A surgical apparatus as recited in claim 2, wherein the notch is formed in a side wall of the carrier channel adjacent a proximal end thereof.

6. A surgical apparatus as recited in claim 5, wherein the second locking member includes a ramped tab extending from the cam bar retainer.

7. A surgical apparatus as recited in claim 6, wherein the aperture is defined in a clasp portion formed integral with the carrier channel.

8. A surgical apparatus as recited in claim 7, wherein the clasp portion includes first and second apertures, wherein the ramped tab is positioned in the first aperture when the cam bar retainer is in the pre-fired proximal position and is positioned in the second aperture proximal of the first aperture when the cam bar retainer is retracted to a post-fired proximal position.

9. A surgical apparatus as recited in claim 2, wherein the carrier channel is removably mounted in the cartridge supporting portion.

10. A surgical apparatus comprising:
 a) an elongated carrier channel;
 b) a cartridge disposed in a distal portion of the carrier channel and containing a plurality of surgical fasteners and a plurality of pushers configured to eject the surgical fasteners from the cartridge body;
 c) a cam bar retainer disposed within the carrier channel and configured to translate therein in a longitudinal direction;
 d) an actuator connected to the cam bar retainer for facilitating the longitudinal translation thereof;
 e) at least two elongated cam bars retained by the cam bar retainer and configured to sequentially interact with the pushers as the cam bar retainer translates in a longitudinal direction; and
 f) a shipping lock pivotally mounted to the actuator and configured to releasably engage the carrier channel to maintain the cam bar retainer in a pre-fired proximal position to prevent movement of the cam bar retainer during shipping.

11. A surgical apparatus as recited in claim 10 further comprising a firing locking mechanism extending from the cam bar retainer and configured to lockingly engage a clasp depending from the carrier channel to maintain the cam bar retainer in a post-fired proximal position.

12. A surgical apparatus as recited in claim 11, wherein the clasp is formed integral with the carrier channel and includes an aperture for receiving and retaining the locking mechanism.

13. A surgical apparatus as recited in claim 12, wherein the clasp includes first and second apertures and, wherein the locking mechanism is positioned in the first aperture when the cam bar retainer is in the pre-fired proximal position and is positioned in the second aperture proximal of the first aperture when the cam bar retainer is retracted to the post-fired proximal position.

14. A surgical apparatus as recited in claim 10, wherein the shipping lock includes a release button pivotably mounted to the actuator.

15. A surgical apparatus as recited in claim 14, wherein the shipping lock includes a retention bar cooperating with the pivoting release button.

16. A surgical apparatus as recited in claim 15, wherein the release button has a camming surface configured to displace the retention bar to release the cam bar retainer.

17. A surgical apparatus as recited in claim 10, further comprising a notch formed in a side wall of the carrier channel adjacent a proximal end thereof for releasably retaining the shipping lock when the cam bar retainer is in the pre-fired proximal position.

18. A surgical apparatus as recited in claim 17, wherein the pre-fired proximal position is distal of the post-fired proximal position.

19. A surgical apparatus comprising:
 a) a cartridge supporting portion having a cartridge disposed therein which contains a plurality of surgical fasteners and a plurality of pushers configured to eject the surgical fasteners from the cartridge;
 b) an anvil supporting portion relatively movable with respect to the cartridge supporting portion and having an anvil surface against which the surgical fasteners are driven when they are ejected from the cartridge;
 c) a cam bar retainer operatively associated with the cartridge and retaining at least two cam bars configured to sequentially interact with the pushers as the cam bar retainer translates distally from a pre-fired proximal position;
 d) an actuator connected to the cam bar retainer for facilitating the translation thereof;
 e) a clasp positioned in the cartridge supporting portion and having first and second slots; and
 f) a detent extending from the cam bar retainer and positioned in the first slot when the cam bar retainer is in the pre-fired proximal position and positioned in the second slot when the cam bar retainer is retracted to a post-fired proximal position, wherein the engagement of the detent in the second slot prevents distal movement of the cam bar retainer.

20. A cartridge assembly as recited in claim 19, wherein in the post-fired proximal position of the cam bar retainer is proximal of the pre-fired proximal position.

21. A surgical apparatus as recited in claim 20, further comprising an elongated carrier channel supported within the cartridge supporting portion and carrying the cartridge, the cam bar retainer, and the cam bars.

22. A cartridge assembly as recited in claim 21, wherein the clasp is formed integral with the carrier channel.

23. A surgical apparatus as recited in claim 19, further comprising an interlock mechanism configured to maintain the cam bar retainer in a pre-fired proximal position so as to prevent premature actuation of the apparatus, the interlock mechanism including a release button pivotably mounted to the actuator.

24. A surgical apparatus as recited in claim 23, wherein the interlock mechanism includes a retention bar configured to releasably engage a notch provided in the carrier channel, and wherein the release button includes a camming surface configured to displace the retention bar from engagement with the notch.

* * * * *